US010111729B1

(12) United States Patent
Lowe et al.

(10) Patent No.: US 10,111,729 B1
(45) Date of Patent: Oct. 30, 2018

(54) NIGHT TIME ORTHODONTICS

(71) Applicant: ORTHOACCEL TECHNOLOGIES INC., Bellaire, TX (US)

(72) Inventors: Michael K Lowe, Bellaire, TX (US); Tamsen Valoir, Houston, TX (US)

(73) Assignee: OrthoAccel Technologies, Inc., Bellaire, TX (US)

( * ) Notice: Subject to any disclaimer, the term of this patent is extended or adjusted under 35 U.S.C. 154(b) by 6 days.

(21) Appl. No.: 15/215,356

(22) Filed: Jul. 20, 2016

Related U.S. Application Data (63) Continuation-in-part of application No. 13/609,346, filed on Sep. 11, 2012, now Pat. No. 9,943,380, and
(Continued)

(51) Int. Cl.
| | |
|---|---|
| *A61C 3/00* | (2006.01) |
| *A61C 7/00* | (2006.01) |
| *A61C 7/08* | (2006.01) |
| *A61N 2/02* | (2006.01) |
| *A61N 5/06* | (2006.01) |
| *A61N 2/06* | (2006.01) |
| *A61C 3/03* | (2006.01) |
| *A61B 17/16* | (2006.01) |

(Continued)

(52) U.S. Cl.
CPC .......... *A61C 7/008* (2013.01); *A61B 17/1604* (2013.01); *A61C 3/03* (2013.01); *A61C 7/08* (2013.01); *A61C 19/06* (2013.01); *A61N 2/02* (2013.01); *A61N 2/06* (2013.01); *A61N 5/062* (2013.01); *A61N 2005/0606* (2013.01); *A61N 2005/067* (2013.01); *A61N 2005/0659* (2013.01)

(58) Field of Classification Search
CPC .. A61C 7/008; A61C 7/08; A61C 7/00; A61C 7/36
USPC .......... 433/6, 18, 24, 118, 119, 122
See application file for complete search history.

(56) References Cited

U.S. PATENT DOCUMENTS 1,826,434 A * 10/1931 Reiss ............... A61C 17/20
601/86
4,123,844 A * 11/1978 Kurz ............... A61C 7/008
433/5
(Continued)

FOREIGN PATENT DOCUMENTS

| JP | 2004321498 | 11/2004 |
|---|---|---|
| WO | WO2001078217 | 10/2001 |

OTHER PUBLICATIONS

Chung How Kau, et al., The clinical evaluation of a novel cyclical force generating device [AcceleDent®] in orthodontics, Orthodontic Practice 1(1): 10-15 (2010).
(Continued)

*Primary Examiner* — Matthew Nelson
(74) *Attorney, Agent, or Firm* — Boulware & Valoir (57) ABSTRACT

Night time use of removable orthodontic appliances coupled with night time use of accelerated orthodontic treatment modalities is provided. Accelerated orthodontic treatment modalities include micropulse vibrations, ultrasound vibrations, photobiomodulation, IR light, low-level laser therapy, pulsed EM fields, static magnetic fields, resonance vibrations, indirect electric current, direct electric current, pharmacological accelerators, surgical accelerators, decortication, osteoperforation, alveocentesis, and piezocision.

19 Claims, 7 Drawing Sheets

Related U.S. Application Data a continuation-in-part of application No. 12/615,049, filed on Nov. 9, 2009, now Pat. No. 9,028,250, and a continuation-in-part of application No. 11/773,849, filed on Jul. 5, 2007, now Pat. No. 9,668,828.

(60) Provisional application No. 62/196,758, filed on Jul. 24, 2015, provisional application No. 62/195,929, filed on Jul. 23, 2015, provisional application No. 60/906,807, filed on Mar. 14, 2007.

(51) Int. Cl.
*A61C 19/06* (2006.01)
*A61N 5/067* (2006.01)

(56) References Cited

U.S. PATENT DOCUMENTS

| | | | |
|---|---|---|---|
| 4,244,688 A | 1/1981 | Kurz | |
| 4,348,177 A | 9/1982 | Kurz | |
| 4,382,780 A | 5/1983 | Kurz | |
| 4,764,111 A * | 8/1988 | Knierim | A61C 7/00 340/309.7 |
| 5,030,098 A * | 7/1991 | Branford | A61H 23/00 433/215 |
| 5,496,256 A * | 3/1996 | Bock | A61C 8/00 433/174 |
| 5,554,971 A | 9/1996 | Foster et al. | |
| 5,774,425 A * | 6/1998 | Ivanov | A61C 7/00 368/11 |
| 5,780,958 A | 7/1998 | Strugach et al. | |
| 5,967,784 A * | 10/1999 | Powers | A61C 7/00 433/2 |
| 6,089,864 A * | 7/2000 | Buckner | A61F 5/56 433/6 |
| 6,613,001 B1 * | 9/2003 | Dworkin | A61C 7/00 600/590 |
| 6,632,088 B2 | 10/2003 | Voudouris | |
| 6,648,639 B2 | 11/2003 | Mao | |
| 6,832,912 B2 * | 12/2004 | Mao | A61C 7/22 433/24 |
| 6,870,304 B2 | 3/2005 | Magnussen et al. | |
| 7,029,276 B2 * | 4/2006 | Mao | A61C 7/00 433/24 |
| 7,296,318 B2 * | 11/2007 | Mourad | A46B 15/0002 15/22.1 |
| 8,152,521 B2 | 4/2012 | Yamamoto et al. | |
| 2004/0013993 A1 * | 1/2004 | Ito | A61C 7/00 433/6 |
| 2004/0063073 A1 * | 4/2004 | Kajimoto | A61C 8/0006 433/215 |
| 2005/0202363 A1 * | 9/2005 | Osterwalder | A61C 9/0006 433/29 |
| 2006/0166157 A1 * | 7/2006 | Rahman | A61B 5/4833 433/6 |
| 2006/0287620 A1 | 12/2006 | Tseng | |
| 2007/0065768 A1 * | 3/2007 | Nadav | A61C 7/006 433/6 |
| 2007/0103016 A1 | 5/2007 | Park et al. | |
| 2007/0161461 A1 | 7/2007 | Nguyun | |
| 2007/0161931 A1 | 7/2007 | Kunita et al. | |
| 2007/0179414 A1 | 8/2007 | Imboden et al. | |
| 2007/0208284 A1 | 9/2007 | Huang | |
| 2007/0255188 A1 | 11/2007 | Tseng | |
| 2007/0299372 A1 | 12/2007 | Chang | |
| 2008/0129130 A1 | 6/2008 | Mun | |
| 2008/0227046 A1 | 9/2008 | Lowe et al. | |
| 2008/0233541 A1 * | 9/2008 | De Vreese | A61C 19/003 433/216 |
| 2008/0273391 A1 * | 11/2008 | Steedman | G11C 5/147 365/185.18 |
| 2009/0051312 A1 | 2/2009 | Simon | |
| 2009/0058361 A1 | 3/2009 | John | |
| 2009/0224616 A1 | 9/2009 | An | |
| 2013/0059263 A1 * | 3/2013 | Lowe | A61C 7/00 433/6 |
| 2013/0095446 A1 * | 4/2013 | Andreiko | A61C 7/08 433/6 |
| 2013/0122448 A1 * | 5/2013 | Kitching | A61C 7/002 433/24 |
| 2013/0252193 A1 * | 9/2013 | Bowman | A61C 7/08 433/6 |
| 2013/0266906 A1 * | 10/2013 | Soo | A61C 7/10 433/6 |
| 2013/0280671 A1 * | 10/2013 | Brawn | A61N 5/0603 433/24 |
| 2014/0004476 A1 * | 1/2014 | Matty | A61C 7/08 433/6 |
| 2014/0080084 A1 * | 3/2014 | Soo | A61C 7/00 433/7 |
| 2015/0125806 A1 * | 5/2015 | Miller | A61C 7/00 433/24 |
| 2015/0224305 A1 * | 8/2015 | Davidovitch | A61N 1/205 433/6 |
| 2015/0231179 A1 * | 8/2015 | Sahin | A61K 35/28 433/24 |
| 2016/0081768 A1 * | 3/2016 | Kopelman | A61C 7/10 433/6 |

OTHER PUBLICATIONS

Kopher RA and Mao JJ. Suture growth modulated by the oscillatory component of micromechanical strain. 2003. J. Bone and Min Res. 18 (3). pp. 521-528.

Nishimura et. al. Periodontal tissue activation by vibration: Intermittent stimulation by resonance vibration accelerates experimental tooth movement in rats. 2008. Am J Orthod Dentofacial Orthop 133(4) pp. 572-583.

Peptan AI, et. al. Responses of intramembranous bone and sutures upon in-vivo cyclic tensile and compressive loading. 2008. Bone (42) pp. 432-438.

Vij K. and Mao, JJ. Geometry and cell density of rat craniofacial sutures during early postnatal development and upon in-vivo cyclic loading. 2006. Bone (38) pp. 722-730.

Krishtab et al., [Use of vibratory action on the teeth to accelerate orthodontic treatment] [Article in Russian] Stomatologiia (Mosk). May-Jun. 1986; 65(3):61-3.

Alikhani, M., et al., "Osteogenic Effect of High-frequency Acceleration on Alveolar Bone," J.D.R. 91: 413 (2012).

Long H. et al., Interventions for accelerating orthodontic tooth movement: A systematic review, The Angle Orthodontist 83(1): 164-171 (2013).

Thiruvenkatachari B., et al., Measuring 3-dimensional tooth movement with a 3-dimensional surface laser scanner. Am J Orthod Dentofacial Orthop. 135(4):480-5 (2009).

Yao, C.C., How to Stimulate Orthodontic Tooth Movement in a non-invasive way: LLLT, online at aaoinfo.org.

\* cited by examiner

| Study | Study Design | Participants | Intervention | Start Time of Orthodontic Tooth Movement After Surgery | Anchorage Augmentation | Outcome |
|---|---|---|---|---|---|---|
| Cruz et al. 2004 | RCT | 11 participants (12–18 y) | Low-level laser therapy[a] | Not specified | Modified Nance arch and transpalatal arch | Effective ($P < .001$) |
| Limpanichkul et al. 2006 | RCT | 12 participants (20.11 ± 3.40 y) | Low-level laser therapy[a] | At least 3 mo after the extraction of first premolars | Vertical loops just mesial to molar tubes | Not effective ($P = .77 > .05$) |
| Fischer 2007 | RCT | 6 participants (11.1–12.9 y) | Corticotomy[a] | 2 wk after surgical exposure | Not specified | Effective ($P = .001$) |
| Gui and Qu 2008 | Quasi-RCT | 20 participants (12–17 y) | Low-level laser therapy[a] | Not specified | Nance arch | Effective ($P < .01$) |
| Kim et al. 2008 | RCT | 7 participants (mean: 20.25 y) | Electrical stimulation[a] | Not specified | Mini-screw | Effective ($P = .003$) |
| Kharkar et al. 2010 | Quasi-RCT | 12 participants (17–22 y) | Dentoalveolar distraction vs periodontal distraction[b] | Dentoalveolar distraction: 2 d after first premolar extraction. Periodontal distraction: immediately after first premolar extraction | Not specified | Dentoalveolar distraction is more effective than periodontal distraction ($P < .01$) |
| Showkatbakhsh et al. 2010 | RCT | 10 participants (23.0 ± 3.3 y) | Pulsed electromagnetic fields[a] | Not specified | Tip back and molar stoppage | Effective ($P < .001$) |
| Aboul-Ela et al. 2011 | RCT | 13 participants (mean: 19 y) | Corticotomy[a] | Immediately after corticotomy | Mini-screw | Effective ($P \leq .01$) |
| Sousa et al. 2011 | RCT | 10 participants (10.5–20.2 y) | Low-level laser therapy[a] | 3 mo after the extraction of first premolars | Not specified | Effective ($P < .001$) |

[a] Interventions were assigned to either the left or right side in the same participant (comparison: intraparticipant).
[b] Interventions were assigned to both sides of different participants (comparison: interparticipant).

FIGURE 7

Laser parameters low energy density

| | | | | |
|---|---|---|---|---|
| Youssef 2008 Syria | GaAlAs semiconductor diode laser | 809 nm  8 J/cm² | 100 mW  80 s/tooth | Days 0, 3, 7, 14 of every stage(3 weeks) For 3 stages |
| Cruz 2004 Brazil | GaAlAs semiconductor diode laser | 780 nm  5 J/cm² | 20 mW  100 s/tooth | Days 0, 3, 7, 14 of each month For 2 months |
| Wang 2007 China | GaAlAs semiconductor diode laser | 780 nm  5 J/cm² | 20 mW  100 s/tooth | Once a week For 8 weeks |
| Sousa 2011 Brazil | GaAlAs semiconductor diode laser | 780 nm  5 J/cm² | 20 mW  100 s/tooth | Days 0, 3, 7 of each month For 4 months |
| Xu 2008 China | He-Ne laser with $CO_2$ laser assisted | 632 nm  2.5 J/cm² | 20 mW | Days 1, 2, 3, 4, 5 in 21 days |
| Fujiyama 2008 Japan | $CO_2$ laser, 5 pulses per 1,000 s | Not specified | 2 W | Once (immediately after separation) |

NIGHT TIME ORTHODONTICS

PRIOR RELATED APPLICATIONS

This application is a Continuation-in-Part of US20080227046 (Ser. No. 11/773,849) (pending), filed Jul. 5, 2007, which claims priority to 60/906,807, filed Mar. 14, 2007, as well as US20100055634 (Ser. No. 12/615,049) (issued as U.S. Pat. No. 9,028,250), filed Nov. 9, 2009, and Ser. No. 13/609,346, filed Sep. 11, 2012 (pending), each of which is incorporated in its entirety herein for all purposes.

This application also claims priority to U.S. Ser. No. 62/195,929, filed Jul. 23, 2015, and 62/196,758, filed Jul. 24, 2015, each incorporated by reference herein in its entirety for all purposes.

FIELD OF THE DISCLOSURE

The disclosure relates to a new method of orthodontic treatment wherein removable orthodontic appliances are worn only at night, but their use is combined with vibration or other orthodontic accelerator to speed orthodontic tooth movement.

BACKGROUND OF THE DISCLOSURE

A malocclusion is a misalignment of teeth or incorrect relation between the teeth of the two dental arches. The term was coined by Edward Angle, the "father of modern orthodontics," as a derivative of occlusion, which refers to the way opposing teeth meet. Angle based his classifications of malocclusions on the relative position of the maxillary first molar. According to Angle, the mesiobuccal cusp of the upper first molar should align with the buccal groove of the mandibular first molar. The teeth should all fit on a line of occlusion, which is a smooth curve through the central fossae and cingulum of the upper canines, and through the buccal cusp and incisal edges of the mandible. Any variations therefrom results in malocclusion.

There are three classes of malocclusions, Class I, II, and III. Further, class II is subdivided into three subtypes:

Class I: Neutrocclusion Here the molar relationship of the occlusion is normal or as described for the maxillary first molar, but the other teeth have problems like spacing, crowding, over or under eruption, etc.

Class II: Distocclusion (retrognathism, overjet) In this situation, the upper molars are placed not in the mesiobuccal groove, but anteriorly to it. Usually the mesiobuccal cusp rests in between the first mandibular molars and second premolars. There are two subtypes:

Class II Division 1: The molar relationships are like that of Class II and the anterior teeth are protruded.

Class II Division 2: The molar relationships are class II but the central incisors are retroclined and the lateral incisors are seen overlapping the central incisors.

Class III: Mesiocclusion (prognathism, negative overjet) In this case the upper molars are placed not in the mesiobuccal groove, but posteriorly to it. The mesiobuccal cusp of the maxillary first molar lies posteriorly to the mesiobuccal groove of the mandibular first molar. This malocclusion is usually seen when the lower front teeth are more prominent than the upper front teeth. In such cases, the patient very often has either a large mandible or a short maxillary bone.

Orthodontics is a dental specialty that treats malocclusion through the movement of teeth as well as the control and modification of facial growth. This process is usually accomplished by using a continuous mechanical force to induce bone remodeling, thereby enabling the teeth to move to a better position. In this approach, orthodontic appliances provide a continuous static force to the teeth via an archwire connected to brackets affixed to each tooth or via a removable appliance such as an aligner, or some similar accessory, that fits over the dentition. As the teeth slowly move due to the orthodontic force, the force is dissipated. The archwires are adjusted to add additional force and to continue the desired tooth movement. Although effective, this widely accepted approach takes about twenty-four months on average to achieve success.

Researchers have long postulated that a pulsating force might also be used to move teeth more rapidly and to ease the discomfort of traditional orthodontics, but Mao was probably the first to prove that the use of cyclic forces could speed bone remodeling in rabbits (see U.S. Pat. No. 6,684,639, U.S. Pat. No. 6,832,912, U.S. Pat. No. 7,029,276). Certain dynamic loading patterns (cycling force with rest periods) were shown to greatly increase bone formation compared to basic dynamic loading. Inserting rest periods is now known to be especially efficacious as it allows mechanosensitivity to be restored to the bone tissue. A point of diminishing returns is reached within each loading session. Therefore, intermittently loading cyclic force can increase the rate of bone formation significantly.

Although promising, Mao studied rabbit cranial suture closure and facial lengthening, and his results, while suggestive, could not be presumed to apply to humans. In addition, the Mao device was completely unsuitable for clinical testing.

OrthoAccel Technologies Inc., invented the first FDA cleared and commercially successful orthodontic vibrating device, as described in US20080227046, designed to apply cyclic forces to the dentition for accelerated remodeling purposes. Both intra-oral and extra-oral embodiments are described in US20080227046, each having processors to capture and transmit patient usage information. The bite plate was specially designed to contact occlusal as well as lingual and/or facial surfaces of the dentition, and thus was more effective than any prior art devices in conveying vibrational forces to the teeth.

Further, the device was tested in clinical trials and shown to speed orthodontic remodeling as much as 50%. Thus, it is truly a breakthrough in orthodontic technology. Finally, the device is slim, capable of hands free operation, lacks the bulky head gear of the prior art devices, and has optimized force and frequency for orthodontic remodeling and only requires 20 minutes usage per night for clinical efficacy. Thus, its comfort level and compliance was also found to be high, with patients reporting that they liked the device, especially after the motor was redesigned to be quieter and smoother, as described in US2010055634 et seq.

In fact, this device has been marketed as AcceleDent® in several countries and has achieved remarkable commercial success since its introduction. AcceleDent® represents the first successful clinical approach to accelerate orthodontic tooth movement by modulating bone biology in a non-invasive and non-pharmacological manner.

One of the interesting side effects in using the AcceleDent® with thousands of patients, is that the orthodontist with the experience and savvy to capitalize on the faster bone remodeling are able to change their treatment plans accordingly. Thus, many practitioners are changing aligner trays every 5-7 days instead of the recommended 14 days, and the patient are thus able to fully realize the decreased treatment time.

However, the basic paradigm of 22-7 aligner usage has not changed. Aligners are cleared for usage the entire day and night, being removed only to eat and brush. Practitioners do not recommend night time-only use, and indeed, most actively counsel against it, noting that the treatment times may be correspondingly increased or that treatment gains can even be reversed during the period of non-use.

This disclosure turns that paradigm around and provides night time usage of aligner, but only when coupled with micropulse vibration or another accelerator modality.

SUMMARY OF THE DISCLOSURE

The disclosure generally relates to a novel treatment modality for removable orthodontic appliances. Fixed appliances, such as braces, are worn 24/7, but the patient has no choice since the devices can only be removed by an orthodontist in a clinical setting. Removable appliances, by contrast, can be removed by patients, and indeed frequently are, resulting in poor outcomes or delayed outcomes.

For example, clear aligners (e.g., Invisalign®, Clear Correct®, and the like), are to be used about 22 hrs per day, seven days a week for efficacy, being removed only for eating and brushing. Indeed, most orthodontists advise patients that if they wear their aligners only at night, their teeth are likely to return to their original positions. By contrast, retainers may be worn only at night, but of course, retainers are used after treatment is concluded to "retain" the teeth in their final desired position, and are not used for remodeling per se. Further, with certain unstable orthodontic cases, even retainers may be fixed and used 24/7.

Certain patients, such as young adults having orthodontic treatment for a special event, such as a wedding or graduation, are highly motivated and have good compliance and thus outcomes. However, for younger patients, especially middle school patients, compliance continues to be a problem. Indeed, many parents are frustrated to learn from the orthodontist that s/he suspects the child is wearing the aligners only until the parent drops the child off at school and then again on returning home. Headgear, such as the orthodontic facemask and reverse-pull headgear, are another type of removable appliance that children hate to wear, and compliance with headgear use is particularly low. Other removable appliances include the Andresen appliance, the medium opening activator (a modified version of the Andresen appliance), the Bionator, the Clark twin block, the spring aligner or Inman aligner, the expansion and labial segment alignment appliance or "ELSAA," and the like.

Thus, there is a market for patients who might wear aligners, headgear, and other removable appliances if they only had to wear the appliance at night. Yet, usage for ⅓ of a day is likely to seriously extend treatment time and conventional wisdom counsels against this type of usage. Treatment time may not extend as much as 3 fold, but 50-100% increases are expected. Thus, a year long treatment plan for an easy case may take two years to accomplish if the appliance is used only at night. Additionally, for certain cases, treatment gains may actually regress during the day when no device is worn, particularly in unstable cases.

We suggest for the first time that night time use is practical, when combined with AcceleDent® treatment e.g., before bed, on wakening, or both, and this is because the micropulses activate bone remodeling at a time when bone remodeling is likely to be higher anyway. Such a treatment modality would be a breakthrough in orthodontics because as many as 50%-75% of the population could benefit from orthodontic treatment, yet avoids it due to pain and poor aesthetics during treatment. A large portion of the untreated population might become amenable to treatment if a more convenient night-time only treatment were proven to be efficacious, and the micropulse treatment is already known to nearly eliminate the pain of treatment.

There is theoretical support for night time treatment with micropulses as a plausible treatment modality because several aspects of the biology of bone remodeling are increased at night. It is known, for example, that eruption seems to occur during the early hours of sleep, although there is some during the day, especially after meals. Also, preosteoblasts, the immediate proliferating precursors of osteoblasts, synthesize DNA primarily during the environmental light period and divide during the subsequent dark cycle. Less differentiated precursor cells (small nuclei), the proliferating predecessors of preosteoblasts, were in S-phase primarily during the dark period and divided in the following light cycle.

As another example, in a study of seven subjects, a plasma growth hormone or "GH" peak lasting 1.5-3.5 hr appeared with the onset of deep sleep. Smaller GH peaks occasionally appeared during subsequent deep sleep phases. Peak GH secretion was delayed if the onset of sleep was delayed.

Yet another circadian protein is Osteocalcin. Osteocalcin (OC) or bone Gla-protein is the main non-collagen protein of bone matrix, which is primarily synthesized by osteoblasts and odontoblasts and hypertrophic chondrocytes. A small amount of OC may be released during bone resorption and measured by some methods, so it could also be called a bone remodeling marker. Circulating OC shows a circadian rhythm with the highest values in the night and the lowest during early morning hours, with the differences reaching up to 50%.

Procollagen I C-Terminal Propeptide or "PICP" is synthesized in osteoblasts as a precursor of collagen type I. PICP values also show a circadian rhythm with amplitude of 20% higher values during the night and lower in the afternoon.

Thus, there is precedent for a significant day versus night difference in bone biology, although no one has yet found a way to capitalize on this, and merely wearing a removable appliance only at night is known to delay favorable outcomes, and even allow the reversal of outcomes.

Vibration is now known to increase bone remodeling, and this has been shown to be true of orthodontic bone remodeling even in humans. The use of 30 Hz, 0.2-0.25 N for 20 minutes daily (about 70% (67%) compliance rate measured) has been clinically shown to speed tooth movement by 50%. Anything that improves the compliance rate may further speed tooth movement.

Alkhani (2012) studied several markers by RT-PCR in sham treated and micropulse treated rats, and found that several orthodontic growth factors all increased, as did the receptors for same, as well as transcription factors, extracellular matrix markers, and mineralization markers all increased in micropulse treated rats as compared to sham treated rats.

The authors suggested that the increased orthodontic remodeling was due to an increase in osteoblast activity rather than cellular proliferation, because the number of osteoblasts per $mm^3$ did not change, although the expression of type I collagen and other non-collagenous matrix proteins increased. This new bone matrix had increased collagen crosslinking, which suggested an acceleration of bone deposition and maturation by resident osteoblasts. Studies in long bones did not produce similar results, but of course, long bones have a different biology than the orthodontic bones.

Thus, nighttime use of aligners coupled with micropulse vibration will activate osteoblast activity, as well as increase several bone growth biomarkers. This increased activity will allow night-time only usage for aligners, which could not heretofore be realized. Clinical results are expected to confirm the proof of action, although not yet available. Our preliminary results suggest efficacy, although considerable work remains before such an indication can be FDA cleared.

By "U-shaped" what is meant herein is that the device follow the curvature of the occlusal surfaces of the dentition, e.g., the biting surfaces of the teeth are in a substantially U-shaped curve.

By "lingually shaped," what is meant is that the device is tongue shaped (e.g., like a U that has been filled in).

When we refer to contacting "the teeth" or similar phrase herein, what is meant is the entire dentition, e.g., the teeth of both arches. If less than the entire dentition is intended, it will be referred to as maxillary teeth, mandibular teeth, or a "portion" of the teeth or specific teeth or arches will be identified by name. Nevertheless, a bite plate need not contact every single tooth, since by definition some malocclusions may result in one or more teeth considerably out of alignment. The phrase also allows some leeway at the molars to accommodate the fact that dentition varies in size, and that molars erupt over 20-25 years of age, if at all, or may be removed to provide additional space for the remaining teeth, and thus most patients will not have a full set of adult teeth. Therefore, a bite plate intended to contact all teeth of the average youth patient, may not reach the molars of older or larger patients, or patients with more mature dentition. It is also understood that if a patient is wearing a removable appliance, such as an aligner, the contact will be indirect, e.g., via the aligners.

A "bite plate" as used herein is a plate worn inside the mouth and generally contacting occlusal surfaces of the teeth, such that the device is held by the patient "biting" on the bite plate. It is not used in its more specialized meaning to refer to devices that correct deep bites by preventing the posterior teeth from touching.

By "aligner" what is meant is a single arch device made by 3D scan or cast that intimately contacts each tooth surface, wherein the position of one or more teeth is adjusted such that the device applies an orthodontic force to that tooth or teeth. Exemplary aligners are available from InvisAlign® and Clear Correct®, and several other companies have entered the market recently. Such devices are intended to be worn at all times, removed only for eating and brushing.

By "wearing an aligner tray" it is understood that the aligner trays come in a series of a plurality of aligner trays with sequential tooth movements programmed thereinto, and that the patient wears one tray at a time in the sequential order provided.

By "treatment modality" what is meant is a mode of action that causes an orthodontic benefit.

By "treatment modality source," what is meant is a device or component of a device that provides the treatment modality. For example, vibration is an orthodontic treatment modality and a vibratory source provides vibration. A vibratory source could also be called a vibrator. Another treatment modality is infrared or ultraviolet light, and an LED or laser could be an exemplary light source.

A "driver" is the hardware component that provides the treatment modality, and in preferred embodiments is a treatment modality source such as a vibrator or laser, a processor, a battery or other power source, and the wiring needed to operatively couple or operate same, contained within a waterproof or at least water resistant housing or coating.

"Orthodontic remodeling" is used herein consistently with its art-accepted definition, and refers to the realigning of teeth by boney remodeling under forces sufficient to provide osteoclastic activity on the high-pressure side, and osteoblastic activity on the reduced-pressure side, but with minimal root resorption, such that teeth are gradually moved and/or realigned to a desired position.

"Orthodontic forces" is used herein consistently with its art-accepted definition, and refers to the steady (static) realigning forces needed for orthodontic remodeling.

By "stable orthodontics" what is meant is a patient whose teeth retain their position for a period of at least 2 years after treatment (with retainer use) or a patient that has average or lower than average levels of markers for orthodontic instability. By contrast, unstable orthodontic patients will regress in a year or two and/or have higher than average levels of biomarkers for orthodontic instability.

"Micropulses" refer herein to the low force, low frequency vibrations that are used to speed orthodontic remodeling. The force ranges from 0.01-5 N and the frequency from 0.1-1000 Hz. It is not yet known if significantly greater frequencies will allow faster orthodontic remodeling, but significantly heavier forces when added to orthodontic forces will likely increase root resorption. Preferred forces are quite low, e.g., about 0.01-0.5 or 0.1-0.3 N or 0.2 N or 0.25N, as are preferred frequencies, e.g., about 10-400 or 20-40 Hz or 30 Hz. Micropulses are now known to cause 50% faster orthodontic remodeling when combined with an orthodontic force.

"Orthodontic remodeling devices" or "orthodontic devices" are used consistently with its art-accepted meaning, and refers to devices that provide orthodontic forces and thus the realigning of teeth. The term includes a variety of devices, such as braces, aligners, positioners, Herbst, saggital appliance, palatal expander, pendulum, Nance, and the like. The term does not include dental cleaning devices, such as electric toothbrushes, or professional cleaning tools such as scalers, and the like, or other equipment that may be used in a dental or orthodontic office.

"Fixed orthodontics appliances" refers to braces, Herbst appliances, and the like that are affixed and removed by a clinician.

"Removable orthodontics appliances" refers to devices used for orthodontic treatment that can be removed by the patient, and include headgear, aligners, and the like, but excluding retainers which are used on completion of orthodontic treatment (and thus are for retention only, not orthodontic treatment).

"Headgear" is used consistently with its art-accepted definition, and refers to various head and neck attachment means used to provide orthodontic forces in a particular direction that cannot be easily be achieved with intra-oral attachment points. These are typically used for severe Class II/III malocclusions.

As used herein "night time usage" or "at night" or similar phrase refers to wearing of the device after school or work in the comfort of one's home, but is not strictly limited to those hours without sunlight, especially since there are few night time hours in the far North during summer. It expressly excludes the traditional 22/7 usage recommended by orthodontists. Furthermore, we refer herein to a recommended usage throughout the treatment plan, as opposed to the occasional night time use that may occur from poor compliance with the standard 22/7 treatment plan.

"Treatment plan" or "entire treatment plan" or similar language refers to a course of treatment or a distinct phase thereof with a set of aligners or other removable appliance during which teeth are moved via orthodontic bone remodeling. In complex treatment plans, there may be more than one phase of treatment, only one of which is amenable to use herein. For example, jaw alignment may need to be corrected before aligner therapy can begin, and the jaw alignment phase may not be amenable to the methods described herein, yet the entire aligner phase may be performed according to these methods. Similarly, the method is applicable to the finishing phase.

As used herein, the "outside edge" of a bite plate is the facial edge of the flat flat, whereas the "inside edge" is the lingual edge. The "rims" on these edges are about perpendicular to the bite plate, thus being able to contact facial and/or lingual surfaces of the teeth or some portion thereof.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated. When used in the context of part dimensions the term "about" includes that degree of tolerance that still allows the parts to operably connect, and thus will vary somewhat based on the flexibility of the material used for the part.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention. Thus, the term consisting essentially of excludes only material elements that change the nature of the invention, such as e.g., bulky headgear, toothbrush bristles, and the like.

The following abbreviations may be used herein:

| | |
|---|---|
| AMBN | ameloblastin |
| ANXA5 | Annexin |
| BMP2 | bone morphogenetic protein 2 |
| COL1A1 | collagen, type I, alpha 1 |
| COL1A2 | collagen, type I, alpha 2 |
| COMP | cartilage oligomeric matrix protein |
| DMP1 | dentin matrix acidic phosphoprotein 1 |
| EGF | Epidermal growth factor |
| ENAM | Enamelin |
| FGF2 | fibroblast growth factor 2 |
| IGF1 | insulin-like growth factor 1 |
| OC | osteocalcin |
| PDGFA | platelet-derived growth factor alpha polypeptide |
| RUNX2 | runt-related transcription factor 2 |
| SMAD1 | SMAD family member 1 |
| SMAD2 | SMAD family member 2 |
| SMAD3 | SMAD family member 3 |
| SMAD4 | SMAD family member 4 |
| TGFB1 | transforming growth factor, beta 1 |

BRIEF DESCRIPTION OF THE DRAWINGS

FIG. 1A-E. Vibration (60 HZ at 0.3 g=0.003 N) induces the expression of bone markers and regulators. Mean "-fold" increases in the expression of osteogenic growth factors (A), growth factor receptors (B), transcription factors (C), extracellular matrix proteins (D), and proteins involved in matrix mineralization (E) are shown for the static group (after 14 days) and the vibration (60 Hz, 0.3 g) group at days 3 and 14. Data are shown as a fold-change in gene expression compared with the untreated group. All data from the 14-day vibration group are significantly different from those of the static group at 14 days and the vibration group at 3 days (from Alikhani, 2012).

FIG. 6 A review of accelerated orthodontic treatment modalities (from Long, 2013).

DETAILED DESCRIPTION

The following are illustrative only and not intended to unduly limit the invention.

In more detail, the invention includes any one or more of the following embodiments, in any combinations thereof:

A method of orthodontic remodeling, said method comprising treating a patient with malocclusions with a removable orthodontic appliance (excluding retainers) that applies orthodontic forces to said patient in order to correct said malocclusions, wherein said patient wears said removable orthodontic appliance only at night during the entire treatment plan (or an entire phase thereof) and combines said wearing with night time usage of a treatment modality that speeds orthodontic remodeling by 50%, said treatment modality being a non-invasive method selected from micropulse vibration, ultrasound vibration, photobiomodulation, IR light, low-level laser therapy (LLLT), pulsed EM fields, static magnetic fields, resonance vibrations, indirect electric current, direct electric current, pharmacological accelerators. It is also possible that an invasive method selected from decortication or corticotomy, osteoperforation or osteotomy, alveocentesis, piezocision, and the like, can be used but this is unlikely to be preferred.

A method of orthodontic remodeling, said method comprising treating a patient with malocclusions with an removable orthodontic appliance (excluding retainers) that applies orthodontic forces to said patient in order to correct malocclusions, wherein said patient wears said removable orthodontic appliance only at night during an entire treatment plan (or entire phase thereof) and combines said wearing with about 20" per night of micropulse vibration at 0.1-400 Hertz (Hz) or 1-100 Hz or 20-40 Hz or 30 Hz and/or 0.01-5 Newtons (N) or 0.1-0.5 N or 0.2-0.3 N. or 0.25 N.

A method wherein said patient has only class I malocclusions and wears an aligner tray.

A method wherein said patient changes aligner trays every week or every 12, 10, 7, or 5 days, or every 4, 3 or 2 days.

A method as herein described wherein said patient is treated for two thirds or half the normal treatment time, but still achieves a desired occlusion because the orthodontic remodeling has significantly increased in speed.

A method as herein described, wherein said patient combines said wearing with about 20" of micropulse vibration in the evening before sleep and in the morning on awakening.

A method as herein described wherein said patient is preselected for having stable orthodontics.

A method as herein described wherein said patient has class II or III malocclusions and wears headgear.

A method as herein described wherein said micropulse vibration is provided by device comprising
an intraoral bite plate comprising:
a substantially U-shaped surface for contacting occlusal surfaces of teeth;
said bite plate having an outside edge having upper and lower rims to contact upper and lower facial surfaces of teeth or at least a portion of teeth;
said bite plate having an inside edge having upper and lower rims to contact at least a portion of upper and lower lingual surfaces of teeth;
an extraoral housing containing a rechargeable battery operably coupled to a vibrator operably coupled to a processor for controlling said vibrator;
said bite plate operably connected to said housing, preferably by snap fit into a socket;
wherein said device is held in place during usage by teeth clamping on the bite plate and lacks other head attachment means; and
said vibrator being able to vibrate at a frequency of 20-40 Hz and at a force of 0.1-0.5 or 0.2-0.25 Newtons.

A method as herein described wherein said micropulse vibration is provided by a device comprising:
an intraoral bite plate comprising:
a substantially U-shaped surface for contacting occlusal surfaces of teeth;
said bite plate having an outside edge having upper and lower rims to contact upper and lower facial surfaces of teeth or at least a portion thereof;
said bite plate having an inside edge having upper and lower rims to contact at least a portion of upper and lower lingual surfaces of teeth;
an extraoral housing containing a rechargeable battery operably coupled to a vibrator operably coupled to a processor for controlling said vibrator and for capturing and transmitting device usage data;
said bite plate operably connected to said housing;
wherein said device is held in place during usage by teeth clamping on the bite plate and lacks other head attachment means; and
said vibrator being able to vibrate at a frequency of 30 Hz and at a force of 0.2-0.25 Newtons.

A method of orthodontic remodeling, said method comprising treating a patient with class I malocclusions with a plurality of aligner trays that apply orthodontic forces to said patient, wherein said patient wears said aligner trays only at night and combines said wearing with about 20" per night of micropulse vibration at 0.1-400 Hz (or 1-100 or 20-40 or 30 Hz) and 0.1-0.5 Newtons (0.25).

A method of orthodontic remodeling, said method comprising treating a patient with class I malocclusions and with stable orthodontics with a plurality of aligner trays that apply orthodontic forces to said patient, wherein said patient wears said aligner trays only at night during an entire treatment plan or entire phase thereof and combines said wearing with about 20" per night of micropulse vibration as herein described wherein said patient changes aligner trays every week until treatment is completed.

A method of orthodontic remodeling, said method comprising treating a patient with class I malocclusions with a plurality of aligner trays that apply orthodontic forces to said patient, wherein said patient wears said aligner trays only at night during an entire treatment plan or entire phase thereof and combines said wearing with about 20" per night of micropulse vibration provided by a device that comprises:
an intraoral bite plate comprising:
a substantially U-shaped surface for contacting occlusal surfaces of teeth;
said bite plate having an outside edge having upper and lower rims to contact upper and lower facial surfaces of teeth;
said bite plate having an inside edge having upper and lower rims to contact at least a portion of upper and lower lingual surfaces of teeth;
an extraoral housing containing a rechargeable battery operably coupled to a vibrator operably coupled to a processor for controlling said vibrator;
said bite plate operably connected to said housing;
wherein said device is held in place during usage by teeth clamping on the bite plate and lacks other head attachment means; and
said vibrator being able to vibrate at a frequency of 20-40 Hz and at a force of 0.1-0.5 Newtons, or 1-1000 Hz and 0.01-0.5 N or some value in that range.

Orthodontic Markers

Alkhani (2012) studied the effect of micropulses in rats on orthodontic marker expression. Sprague-Dawley rats were divided among control, sham, and experimental groups. The experimental group underwent localized accelerations at different frequencies for 5 min/day on the occlusal surface of the maxillary right first molar at a very low magnitude of loading ($4\mu\varepsilon$). Sham rats received a similar load in the absence of acceleration or frequency.

Figure 1A:
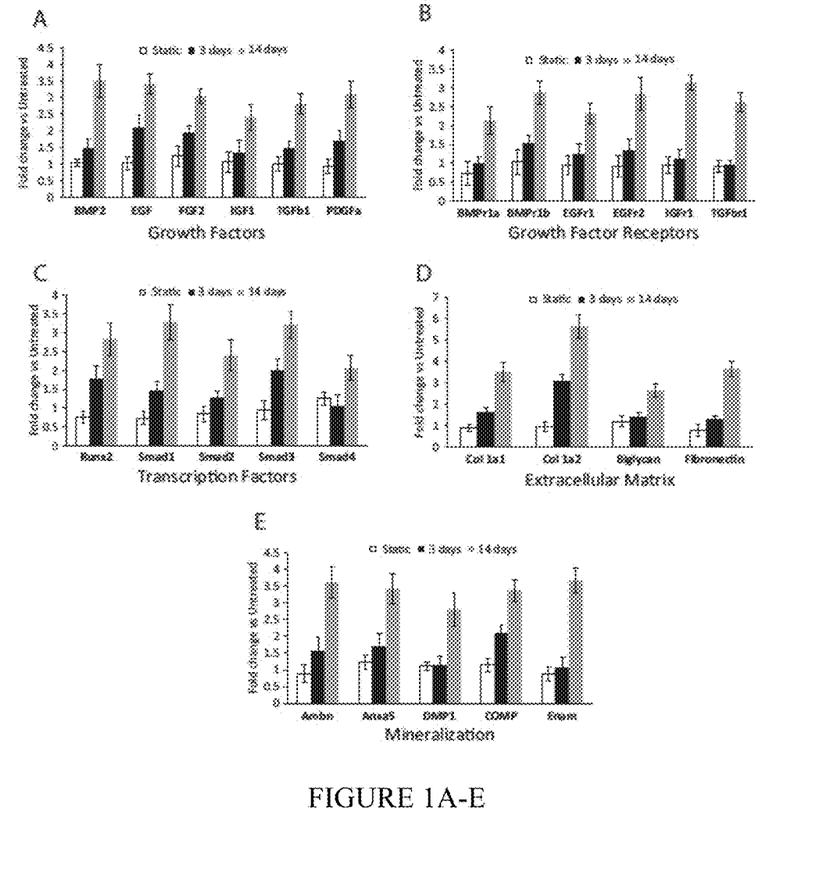

The expression of 92 different osteogenic-related genes by RT-PCR at 0, 3, and 14 days after the micropulse application were studied (FIGS. 1A-E). The expression of 26 genes in the rats that received vibration (0.3 g, 60 Hz) was significantly higher ($p<0.05$) on day 14 compared with that in the static force group. The expression of 6 growth factors (FIG. 1A), 6 growth factor receptors (FIG. 1B), and 5 transcription factors, which play an important role in osteoblast differentiation (FIG. 1C), increased 2- to 3.5-fold. This increase was accompanied by a 2.5- to 6-fold increase in the expression of extracellular matrix proteins (FIG. 1D) and a 2.5- to 3.5-fold increase in the expression of mineralization proteins (FIG. 1E). At day 3, the expression of EGF, FGF2, Collagen I, RUNX2, SMAD3, and COMP expression increased 2- to 3-fold (p<0.05). No differences were observed in the static group between 3 and 14 days.

Growth factors BMP2 EGF, FGF2, IGF1, TGFB1, PDGFA, all increased, as did the receptors for same. Transcription factors RUNX2, SMAD1, SMAD2, SMAD3, and SMAD4 increased, extracellular matrix markers COL1A1, COL1A2, BIGLYCAN, and FIBRONECTIN increased, and mineralization markers AMBN, ANXA5, DMP1, COMP and ENAM all increased in micropulse treated rats as compared to sham treated rats.

Therefore, there is a biological basis for the accelerated orthodontic movement seen with the application of micropulse vibrations. Further, the extent of the increase appears likely to support night-time only usage of orthodontic forces without significant negative impact. It may even be enough to still allow accelerated treatment.

Night Time Treatment of Class 1 Malocclusions

Patients with class 1 occlusion (crowding, incorrect spacing, and lack of extrusion) are examined and an clear aligner treatment plan proposed. Force attachments are used where appropriate for torque or extrusion. Patients are split into two groups, one to wear aligners 22/7 and treat with micropulses for 20" twice a day (morning and evening), and the second group to wear aligners only at night, but again with micropulses.

The micropulse treatment will be with the FDA cleared device known as AcceleDent®, which provides 30 Hz, 0.2-0.25 Newton micropulses. This device has a specially designed bite plate that has upper and lower rims contacting the facial surfaces of the teeth up to at least the canines and some of the lingual surfaces, and thus is able to provide vibration in two axes. Of course, tooth contact will be indirect because the patient wears the aligner during AcceleDent usage.

Normally trays are changed every two weeks, although when combined with AcceleDent®, the trays can be changed every 7 days, 5 days, 3 days, or even as short as two days. For this study, patients will be instructed to change trays when the existing tray no longer seems to impart a force to the teeth, and to keep track of the interval. We anticipate that a 7-day rotation will be sufficient for most patients, although older patients may require increased intervals. To facilitate this treatment plan, patients will be provided with all trays at the start of treatment. The shorter tray usage time is already well established with 24/7 usage, and it is expected that it will also be possible with night-time only usage. However, even if longer tray time is required, the ability to use the aligners only at night while achieving the same orthodontic benefit is still a huge advantage over the prior art.

Teeth are laser scanned at office visits or photographed offsite by the patient and tooth translation, rotation and extrusion measured (Thiruvenkatachari 2009). These patients can also be compared against historical tooth movement rates, which are well established in the literature. On conclusion of treatment, permanent fixed or removable retention will be used, according to the recommendations of the treating orthodontist. However, it is expected that there may be a preference for vacuum formed retainers (VFRs) in a patient population that is particularly interested in night time only treatment.

Patients will be followed throughout the treatment plan, as well as at 6 month intervals thereafter, and stability ascertained. It is anticipated that there will be patients with reduced stability for whom this treatment will be less effective than the recommended 22/7 treatment. However, those studies that have attempted to study stability have been inconclusive, and there is as yet no way to conclusively determine in advance which patients will show lack of stability. Researchers continue to study stability, and it is anticipated that in the near future it will become possible to predict stability in advance based e.g., on bone density or bone marker expression, such as relaxin expression.

At least one study to measure relaxin levels in unstable patients was too small to detect any differences, but its possible that a larger study may prove otherwise. Further, many adult patients with successful and stable orthodontic treatment as teens may nonetheless desire refinement of their orthodontics as adults, and such patients can easily be selected as having stable orthodontics, and adult patients are particularly likely to be interested in night time only treatment options. Thus, it is anticipated that patients may advantageously be preselected for stable orthodontics, and those patients preferentially treated with night-time only removable orthodontic appliances. Patients can alternatively be moved from a 8-12/7 to 22/7 treatment plan if the ongoing measurements indicate that there is an ongoing stability problem.

Night Time Treatment of Class II/III Malocclusions

In a second study, Class II and III occlusions will be treated using aligners coupled with Class II or III correctors. Aligners can be used to treat overjet and underjet, but they are typically cut out at the molars and class II/II appliances, such as the Herbst, added. Alternatively, headgear may be used, and if so, it will be possible to study night time headgear usage as above. Headgear is particularly hated by patients, and night time only use may be a useful accommodation. Patients will be followed and tooth movement rates measured as above.

Micropulse Device

The device is described in more detail in US20080227046, US20100055634 and Ser. No. 13/609, 346, and the various related cases, each of which is incorporated in its entirety herein for all purposes. However, preferred embodiments are described in FIG. 2-5.

Figure 2A:
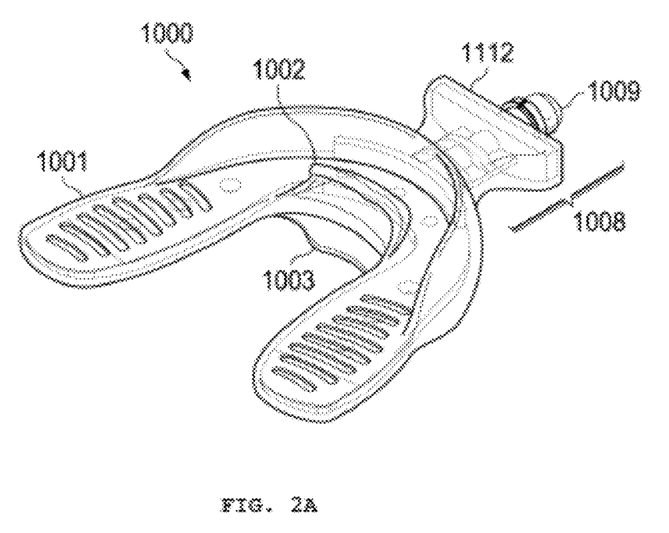
FIGS. 2A and 2B shows a perspective view of a bite plate from two angles, showing the flat U-shaped base, and upper and lower lingual and facials rims, as well as the stem, which fits into a mating socket on the extraoral housing (not shown).
Figure 2B:
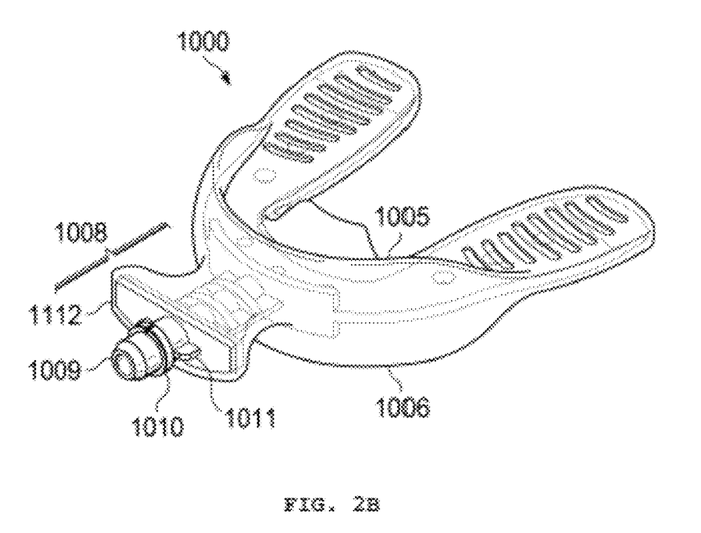

FIG. 2 shows an improved bite plate (1000), having generally U-shaped base (1001) that contacts occlusal surfaces of the teeth, the base having front and back edges, one or both edges having a rim to contact the facial and lingual surfaces of teeth and/or gums. Thus, upper lingual rim (1002), lower lingual rim (1003), upper facial rim (1005) and lower facial rim (1006) are shown. In this instance, the lingual rims contact only the incisors and/or canines, but not the molars. However, the rims can be varied in length to contact all, or a portion, of the teeth. It is preferred that at least one rim contact each tooth (at least up to canines or premolars), except for specially designed bite plates made to correct extreme abnormalities.

Also shown in FIG. 2 is the stem (1008), which is the portion of the bite plate (1000) that mates with a corresponding socket in the extraoral housing (not shown here). In more detail, a cylindrical shaft (1009) is shown, having a groove (see FIG. 3) into which a jump ring (1010) fits, and mates (snap fits) with a corresponding depression in the socket. Optional flare (1112) is also shown, and is configured to provide an appropriate surface so that the user can push the stem into the socket.

The thickness of the biocompatible overlay material can be adjusted to compensate for various patient bite configurations (open, deep, flat), as detailed in UD2010055634, incorporated by reference herein. However, in most instances a bite plate that is slightly thinner at the distal end than the mesial end will accommodate the hinged nature of the temperomandibular joint and facial skeleton.

Thus, if a U-shaped bite plate has two back ends that can contact one or more distal or posterior teeth, and a front end that can contact one or more mesial or anterior teeth, and a thickness E, wherein said thickness E is 2-10 mm, the bite plate can be in one of three configurations:

a) thickness E does not substantially vary from said front end to said back ends;

b) thickness E increases from E at said front end to E plus 0.5-10 mm at said back ends;

c) thickness E increases from E at said back end to E plus 0.5-10 mm towards said front end.

We have shown the stem on the bite plate, but the bite plate may contain the socket, and the extraoral component may have the stem. Further, we have shown a cylindrical shaft with jump ring circumnavigating the shaft (a cylindrical type snap fit), as one example of a reversible coupling mechanism, but any reversible coupling mechanism could be employed, including a cantilevered beam snap fit, a spherical snap-fit, depressible push pins and sockets, a threadable screw fit, and the like.

Figure 3A:
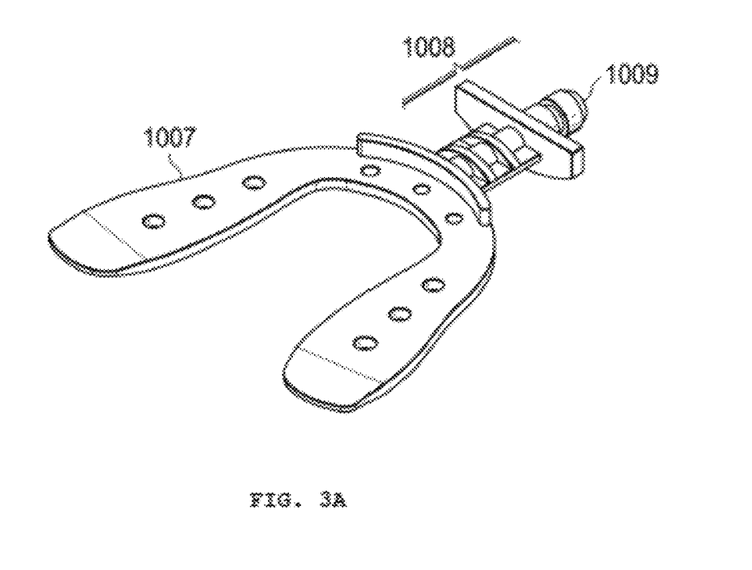
FIGS. 3A and 3B shows the core of the bite plate from two angles, over which is molded a biocompatible overlay having the rims and desired final shape.
Figure 3B:
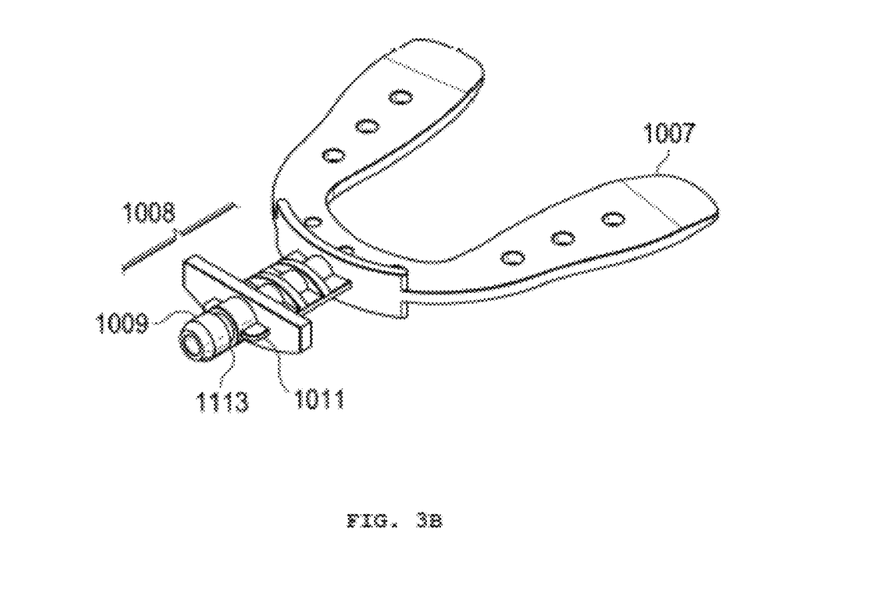

FIG. 3 shows the core (1007) of the bite plate, typically made from a resin, metal or ceramic having a harder durometer than the outer surface, and providing sufficient rigidity to the stem (1008) so as to allow it to lockingly fit into the socket. Cylindrical shaft (1009) has a groove (1113), into which jump ring (1010) fits. Also seen are locking pins (1011) and orientation pins (1114), which prevent the bite plate from being inserted upside down. However, any snap fit, screw fit or other mechanism could be used.

Generally plastics of at least 40 Shore D are used for the core, but metals or ceramics could also be used. A coating is provided over this core, and provides the final shape of the bite plate, as shown in FIG. 2. Such coating should be a biocompatible soft polymer of 40-70 Shore A, and particularly preferred is a medical grade, clear silicone.

Figure 4:
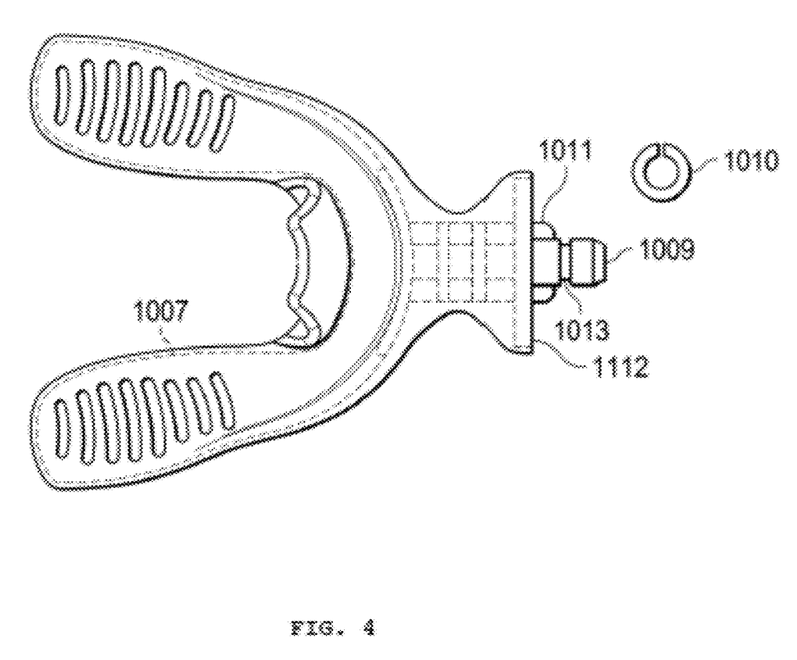
FIG. 4 shows a top view of the bite plate, more clearly illustrating the stem, flare, pins, cylindrical shaft and groove, into which fits the jump ring that mates with a corresponding recess in the socket (not shown).

FIG. 4 shows a top plan view of the bite plate, more clearly illustrating the core (1007), shaft (1009), flare (1112), pins (1011) and jump ring (1010), as well as the other edge of the overcoat, which provides the actual shape of the bite plate.

Figure 5A:
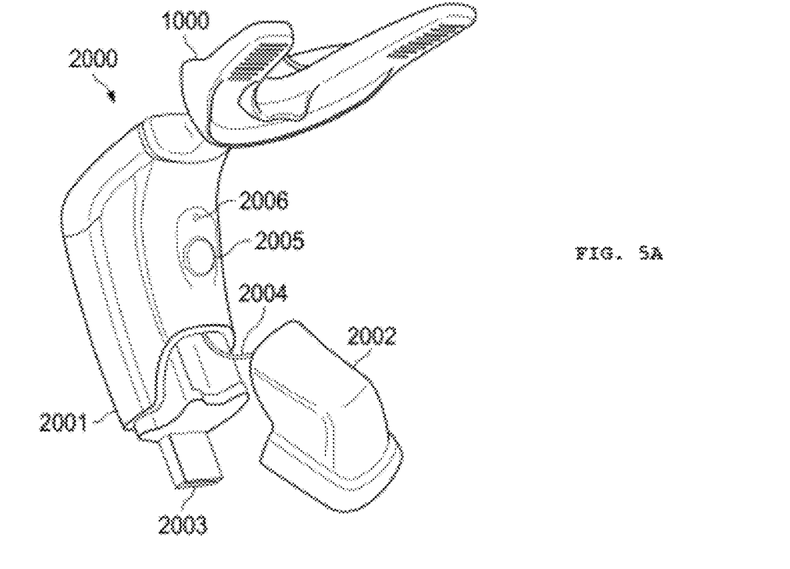
FIGS. 5A and 5B shows a USB embodiment from two angles, wherein the USB is housed inside an access hatch that is tethered to the main body of the housing, and the USB functions for both recharging and data transmission purposes.
Figure 5B:
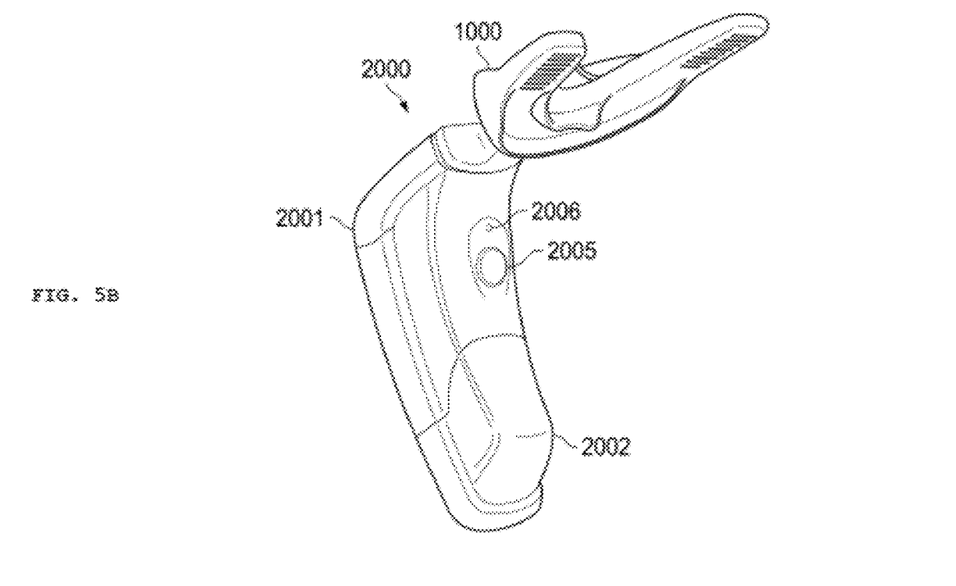

FIG. 5 shows the entire device including the bite plate (1000) and extraoral component (2000). The extraoral component comprises a housing (2001) which is ergonomically and aesthetically shaped, and has an on/off switch (2005), such as a membrane button and LED indicator light (2006). Preferably, both the LED and the on/off switch are contained within the same membrane, as this simplifies manufacturing and improves reliability.

Inside the housing is the battery, processor and vibrator, as described herein and not detailed in FIG. 5. Also shown is an access hatch or cap (2002), that is connected to the body of the housing by tether (2004). This prevents the cap from being lost. By "tether" herein, any form of attachment is meant, including a hinge, or coiled line. Inside the hatch, USB connector (2003) is seen, which functions to both transmit data and to allow charging of a rechargeable battery, which is positioned inside the housing and not accessible to the patient.

In preferred embodiments, the access hatch can only be opened with a tool, e.g., via a small recess and cantilevered snap fit catch. This is preferred because it reduces the regulatory burden, avoiding certain IEC 60601 requirements. Also preferred, the battery is not accessible to the patient, necessitating return to the manufacturer when/if the battery needs replacing. This configuration is desirable as further reducing the regulatory burden, reducing the risk of electrostatic discharge (EDS), and also allowing the manufacturer to reset the system and provide any needed refurbishment when/if the battery is changed. Further, the battery is expected to last throughout the treatment period, and replacements should rarely be required.

The processor collects raw usage data, including date and length of use. A certain amount of java code is contained in the chip, turning the USB into a virtual flash drive, but any suitable code can be used. Thus, when the device is plugged into a computer, the code converts the raw data into suitable graphics.

These graphics need not be available on the device, which may lack a flash drive and thus cannot be misappropriated or overwritten by patients. Instead, the small amount of code embedded in the processor converts the raw data to a usable form when plugged in and activated. This allows the smallest footprint, reduces regulatory burdens, and still provides convenient data analysis in a variety of forms, which can be used by practitioners and in clinical trials. JavaScript code from an open source package was used, called "dygraphs JavaScript Visualization Library" (see code.google.com/p/dygraphs/), but any other code could be used as well.

Setting the time and data on the device may require an external source of communicating to the device. With the device connected to a personal computer the user will navigate to the compliance data report which will display instructions for the user to initiate a file save operation using their browser, which will access the product FLASH drive and enters a file name to save such as "DateTime". The browser will save the compliance report on the product FLASH drive under a given file name. The product will use the file creation date provided by the operating system in the file save operation to set the real time clock in the device.

The cyclic force or vibration applied to the bite plate and thus to teeth is at frequencies between 1 to 1000 Hz (preferably 0.1-400 or 1-100 Hz and most preferred 20-40 Hz or 30 Hz) and a force of 0.01-5 Newtons (or 0.1-0.5 or 0.2 or 0.25 Newtons) for a period of 1-60 minutes, preferably about 1-30 or 1-10 minutes or about 20 minutes. This is followed by a period of recovery, ranging from 2-24 hours, preferably from 8-12 hours, and the cycle is repeated until one or more teeth are successfully moved. Most preferred, the device is used together with the removable orthodontic appliance for 20" in the evening or before bed and again on rising.

More particularly, the micropulse appliance has a vibrational source capable of providing a vibratory force at a frequency of between 20 to 40 Hz or 30 Hz and a force of 0.1-0.5 Newtons or 0.25 Newtons. Excess force is generally unpleasant to the patient, especially force coupled with high frequency. Further, excess force may cause root resorption.

It is known that a smooth, quiet device improves compliance and patient satisfaction, thus a means of feedback control is preferably provided to keep the force and frequency with a few Hz and 0.05 N of the selected values. See e.g., US20100055634, et seq, incorporated by reference herein in its entirety for all purposes.

Other Treatment Modalities

Micropulse vibration provided by AcceleDent® is the first FDA cleared method and device for accelerating orthodontics, but several other treatment modes are under investigation and promising results have been reported. Alternative treatment modalities that can be combined with night time only use of removable appliances include non-invasive methods such as ultrasound vibrations, photobiomodulation such as IR light or low-level laser therapy (LLLT), pulsed EM fields, static magnetic fields, resonance vibrations, indirect electric current, direct electric current, pharmacological accelerators, and the like, as well as invasive methods such as decortication or corticotomy, osteoperforation or osteotomy, alveocentesis, piezocision, and the like. See e.g. Nimiri (2013) and Long (2013), and FIG. 6, as well as the literature cited therein (each incorporated by reference herein in its entirety for all purposes).

Figure 7:
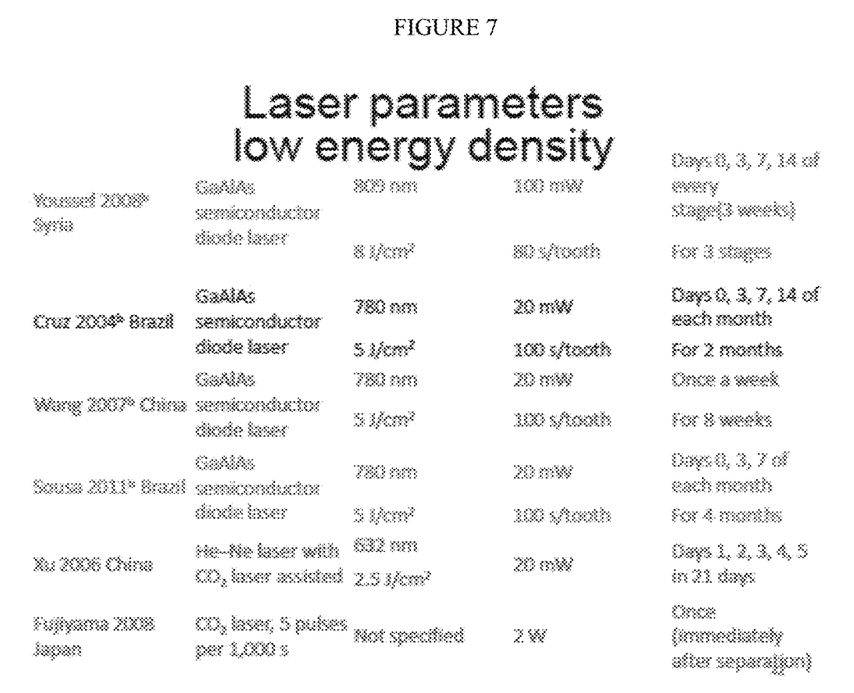
FIG. 7 Low level laser treatment parameters (from Yao, 2015).

The most promising accelerators are LLLT and surgical methods. However, LLLT or other form of photobiomodulation will probably be preferred as being non-invasive. Data available to date suggests that LLLT can be used in place of micropulse vibrations, likely with similar efficacy. See e.g., FIG. 7. For example, one group observed increases in DNA/RNA synthesis at LLLT at 620 nm, 680 nm, 760 nm, and 820 nm when a 560-960 nm range was tested as 1-5 mW/cm$^2$. Others have seen acceleration at 810-830 nm, 780-790 nm, or 970 nm, suggesting a broad range of frequencies can be used. There are definite frequency optima, as expected since the increases are likely due to absorption by specific proteins.

Other studies have observed increases in RANK/RANKL, MMP9, cathepsin K, and integrin on stimulation with LLLT. Interestingly, more than one group has observed that lower energy density (2.5, 5, and 8 J/cm2) was more effective than higher (e.g., 20-25 J/cm$^2$). This shows that there is positive correlation between the dosage and efficacy until reaching a threshold. Once beyond the threshold, higher dosage will not promote, and may only inhibit accelerated orthodontics, possibly through denaturing or otherwise inhibiting the proteins that absorb the light.

Although a light emission diode may emit light with fixed wavelength, it is incoherent in nature and in some studies does not give similar increase of orthodontic tooth movement rate in rats as does a more coherent light source, such as a laser. However, OsseoPulse® is one device being developed for accelerated orthodontics that uses a near-infrared light emitting diode (LED) therapy to accelerate bone remodeling. If such device is eventually shown to have clinical efficacy in accelerating orthodontics, it could also be used in the method.

Many different forms of pharmacotherapy are being evaluated to enhance tooth movement, including injections of vitamin C and D and metabolites, calcitrol, corticosteroids, and many other compounds. This ongoing area of research deserves attention as these advances may become a routine part of treatment. To the extent that such adjuvants accelerate tooth movement, they can be combined with the methods described herein, and can even be used alone if efficacy is sufficiently high.

The following references are expressly incorporated in their entirety:
US20060287620
US20070103016
US20070161461
US20070161931
US20070179414
US20070208284
US20070255188
US20070299372
US20080129130
US20080227046
US20090051312
US20090058361
US20090224616
U.S. Pat. No. 4,244,688
U.S. Pat. No. 4,348,177
U.S. Pat. No. 4,382,780
U.S. Pat. No. 5,030,098
U.S. Pat. No. 5,554,971
U.S. Pat. No. 5,780,958
U.S. Pat. No. 5,967,784
U.S. Pat. No. 6,632,088
U.S. Pat. No. 6,684,639
U.S. Pat. No. 6,832,912
U.S. Pat. No. 6,870,304
U.S. Pat. No. 7,029,276
U.S. Pat. No. 8,152,521 by Yamamoto
JP2004321498 by Yamashiro
WO2001078217
Alikhani, M., et al., "Osteogenic Effect of High-frequency Acceleration on Alveolar Bone," J. D. R. 91: 413 (2012).
Kau, C. H., et al., The clinical evaluation of a novel cyclical force generating device [AcceleDent®] in orthodontics, Orthodontic Practice 1(1): 10-15 (2010).
Kopher R. A. and Mao J. J. Suture growth modulated by the oscillatory component of micromechanical strain. 2003. J. Bone and Min Res. 18 (3). pp. 521-528.
Krishtab et al., [Use of vibratory action on the teeth to accelerate orthodontic treatment] [Article in Russian] Stomatologiia (Mosk). 1986 May-June; 65(3):61-3.
Long H. et al., Interventions for accelerating orthodontic tooth movement: A systematic review, The Angle Orthodontist 83(1): 164-171 (2013).
Nimeri et al. Acceleration of tooth movement during orthodontic treatment—a frontier in Orthodontics, Progress in Orthodontics 2013, 14:42, online at progressinorthodontics.com/content/pdf/2196-1042-14-42.pdf.
Nishimura et. al. Periodontal tissue activation by vibration: Intermittent stimulation by resonance vibration accelerates experimental tooth movement in rats. 2008. Am J Orthod Dentofacial Orthop 133(4) pp. 572-583.
Peptan A. I., et. al. Responses of intramembranous bone and sutures upon in-vivo cyclic tensile and compressive loading. 2008. Bone (42) pp. 432-438.
Thiruvenkatachari B., et al., Measuring 3-dimensional tooth movement with a 3-dimensional surface laser scanner. Am J Orthod Dentofacial Orthop. 135(4):480-5 (2009).
Vij K. and Mao, J. J. Geometry and cell density of rat craniofacial sutures during early postnatal development and upon in-vivo cyclic loading. 2006. Bone (38) pp. 722-730.
Yao, C. C., How to Stimulate Orthodontic Tooth Movement in a non-invasive way: LLLT, online at aaoinfo.org.

The invention claimed is:

1. A method of orthodontic remodeling, said method comprising treating a patient with malocclusions with aligner trays that apply orthodontic forces to said patient to correct said malocclusions, wherein said patient wears said aligner trays only at night throughout the treatment plan and combines said wearing with 1-20" per night of micropulse vibration, said micropulse vibration shown to speed orthodontic remodeling by 50% as compared with a similar patient not using said micropulse vibration.

2. The method of claim 1, wherein said micropulse vibration is at 0.1-1000 Hz and 0.001-0.5 N.

3. The method of claim 1, wherein said micropulse vibration is at 1-400 Hz and 0.1-0.5 N.

4. The method of claim 1, wherein said patient has only class I malocclusions.

5. The method of claim 4, wherein said patient changes aligner trays every week.

6. The method of claim 4, wherein said patient changes aligner trays every 5 days.

7. The method of claim 1, wherein said patient combines said wearing with 1-20" of micropulse vibration in the evening before sleep and in the morning on awakening.

8. The method of claim 1, wherein said patient is preselected for having stable orthodontics.

9. The method of claim 1, wherein said patient has class II or III malocclusions and wears i) headgear and aligner trays or ii) a Herbst or a Class III corrector and aligner trays.

10. The method of claim 1, wherein said micropulse vibration is provided by device comprising:
   a) an intraoral bite plate comprising:
      i) a substantially U-shaped surface for contacting occlusal surfaces of teeth;
      ii) said bite plate having an outside edge having upper and lower rims to contact upper and lower facial surfaces of at least a portion of teeth;
      iii) said bite plate having an inside edge having upper and lower rims to contact at least a portion of upper and lower lingual surfaces of teeth;
   b) an extraoral housing containing a rechargeable battery operably coupled to a vibrator operably coupled to a processor for controlling said vibrator;
   c) said bite plate operably connected to said housing;
   d) wherein said device is held in place during usage by teeth clamping on the bite plate and lacks other head attachment means; and,
   e) said vibrator being able to vibrate at a frequency of 20-40 Hz and at a force of 0.1-0.5 Newtons.

11. The method of claim 1, wherein said micropulse vibration is provided by a device comprising:
   a) an intraoral bite plate comprising a substantially U-shaped surface for contacting occlusal surfaces of teeth;
   b) an extraoral housing containing a rechargeable battery operably coupled to a vibrator operably coupled to a processor for controlling said vibrator and for capturing and transmitting device usage data;
   c) said bite plate operably connected to said housing;
   d) wherein said device is held in place during usage by teeth clamping on the bite plate and lacks other head attachment means; and,
   e) said vibrator being able to vibrate at a frequency of 30 Hz and at a force of 0.2-0.25 Newtons.

12. A method of orthodontic remodeling, said method comprising treating a patient with class I malocclusions with a plurality of aligner trays that apply orthodontic forces to said patient, wherein said patient wears said aligner trays only at night throughout an entire treatment plan or entire phase thereof and combines said wearing with 1-20" per night of micropulse vibration at 0.1-1000 Hz and 0.001-0.5 Newtons.

13. A method of orthodontic remodeling, said method comprising treating a patient with class I malocclusions and with stable orthodontics with a plurality of aligner trays that apply orthodontic forces to said patient, wherein said patient wears said aligner trays only at night throughout an entire treatment plan or an entire phase thereof and combines said wearing with 1-20" per night of micropulse vibration at 0.1-400 Hz and 0.1-0.5 Newtons, and wherein said patient changes aligner trays at least every week until said entire treatment plan or entire phase thereof is completed.

14. A method of orthodontic remodeling, said method comprising treating a patient with class I malocclusions with a plurality of aligner trays that apply orthodontic forces to said patient, wherein said patient wears said aligner trays only at night throughout an entire treatment plan or entire phase thereof and combines said wearing with 1-20" per night of micropulse vibration provided by a device that comprises:
   a) an intraoral bite plate comprising a substantially U-shaped surface for contacting occlusal surfaces of teeth;
   b) an extraoral housing containing a rechargeable battery operably coupled to a vibrator operably coupled to a processor for controlling said vibrator;
   c) said bite plate operably connected to said housing;
   d) wherein said device is held in place during usage by teeth clamping on the bite plate and lacks other head attachment means; and,
   e) said vibrator being able to vibrate at a frequency between 0.1-400 Hz and at a force between 0.001-0.5 Newtons.

15. A method of orthodontic remodeling, said method comprising treating a patient with malocclusions with aligner tray(s) that applies orthodontic forces to said patient in order to correct said malocclusions, wherein said patient wears said aligner tray(s) only at night during an entire treatment plan or entire phase thereof and simultaneously combines said wearing with a treatment modality that speeds orthodontic remodeling by 50%, said treatment modality being selected from one or more of micropulse vibrations, ultrasound vibrations, photobiomodulation, IR light, low-level laser therapy, pulsed EM fields, static magnetic fields, resonance vibrations, indirect electric current, direct electric current, pharmacological accelerators, surgical accelerators, decortication, osteoperforation, alveocentesis, or piezocision.

16. The method of claim 15, wherein said method is combined with co-administration of one or more pharmacological agents to accelerate orthodontic remodeling.

17. A method of orthodontic remodeling, said method comprising wearing an aligner combined with 1-20" of vibration provided by a device that comprises:
   a) an intraoral bite plate comprising:
      i) a substantially U-shaped surface for contacting occlusal surfaces of teeth;
   b) an extraoral housing containing a power source operably coupled to a vibratory source operably coupled to a processor for controlling said vibratory source;
   c) said bite plate operably connected to said housing;
   d) wherein said device is held in place during usage by teeth clamping on the bite plate and lacks other head attachment means; and,
   e) said device being able to vibrate at a frequency of 0.1-400 Hz;
   f) wherein said patient wears said aligner trays only at night during said treatment period.

18. The method of claim 17, wherein said device vibrates at 20-40 Hz and 0.1-0.5 N.

19. The method of claim 17, wherein said device vibrates at about 30 Hz and about 0.2 N and said device speeds orthodontic remodeling by 50% as compared to a similar patient not using said device.

* * * * *